United States Patent
Cook et al.

(10) Patent No.: US 6,300,495 B1
(45) Date of Patent: Oct. 9, 2001

(54) PROCESS FOR THE PREPARATION OF A METAL SALT OF CLAVULANIC ACID

(75) Inventors: Michael Allen Cook, Nr Lewes; Mazin Nicola, Worthing, both of (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 09/402,231

(22) PCT Filed: Apr. 2, 1998

(86) PCT No.: PCT/EP98/02137

§ 371 Date: Sep. 30, 1999

§ 102(e) Date: Sep. 30, 1999

(87) PCT Pub. No.: WO98/45300

PCT Pub. Date: Oct. 15, 1998

(30) Foreign Application Priority Data

Apr. 4, 1997 (GB) .................................................... 9706846
Jul. 2, 1997 (GB) .................................................... 9713887

(51) Int. Cl.[7] ........................... C07D 503/18; A61P 31/04
(52) U.S. Cl. .............................................................. 540/349
(58) Field of Search ............................................... 540/349

(56) References Cited

U.S. PATENT DOCUMENTS 5,726,170 * 3/1998 Callewaert ............................ 514/210
5,821,364 * 10/1998 Weber ................................... 540/349
5,859,238 * 1/1999 Copar ................................... 540/349
5,985,625 * 11/1999 Capuder ............................... 540/349

FOREIGN PATENT DOCUMENTS

| 0 594 099 A1 | 10/1993 | (EP) . | |
| 0 594 099 B1 | 10/1993 | (EP) . | |
| WO 93/25557 | 12/1993 | (WO) . | |
| WO 94/21647 | 9/1994 | (WO) . | |
| WO 95/21173 | 8/1995 | (WO) | C07D/503/00 |
| WO 95/34194 | 12/1995 | (WO) . | |
| WO 96/28452 | 9/1996 | (WO) | C07D/503/18 |
| WO 97/05142 | 2/1997 | (WO) | C07D/503/00 |

OTHER PUBLICATIONS

"The Aldrich Catalog", Aldrich Chemical Company, Milwaukee, WI, 1992, p. 1655.*

* cited by examiner

Primary Examiner—Mukund J. Shah
Assistant Examiner—Thomas C McKenzie
(74) Attorney, Agent, or Firm—Dara L. Dinner; Stephen Venetianer; Charles M. Kinzig

(57) ABSTRACT

A process for the preparation of a metal salt of clavulanic acid which comprises the reaction between an organic amine salt of clavulanic acid and a metal salt precursor compound, the reaction taking place in a liquid medium which comprises a liquid florinated and/or chlorinated hydrocarbon.

15 Claims, 1 Drawing Sheet

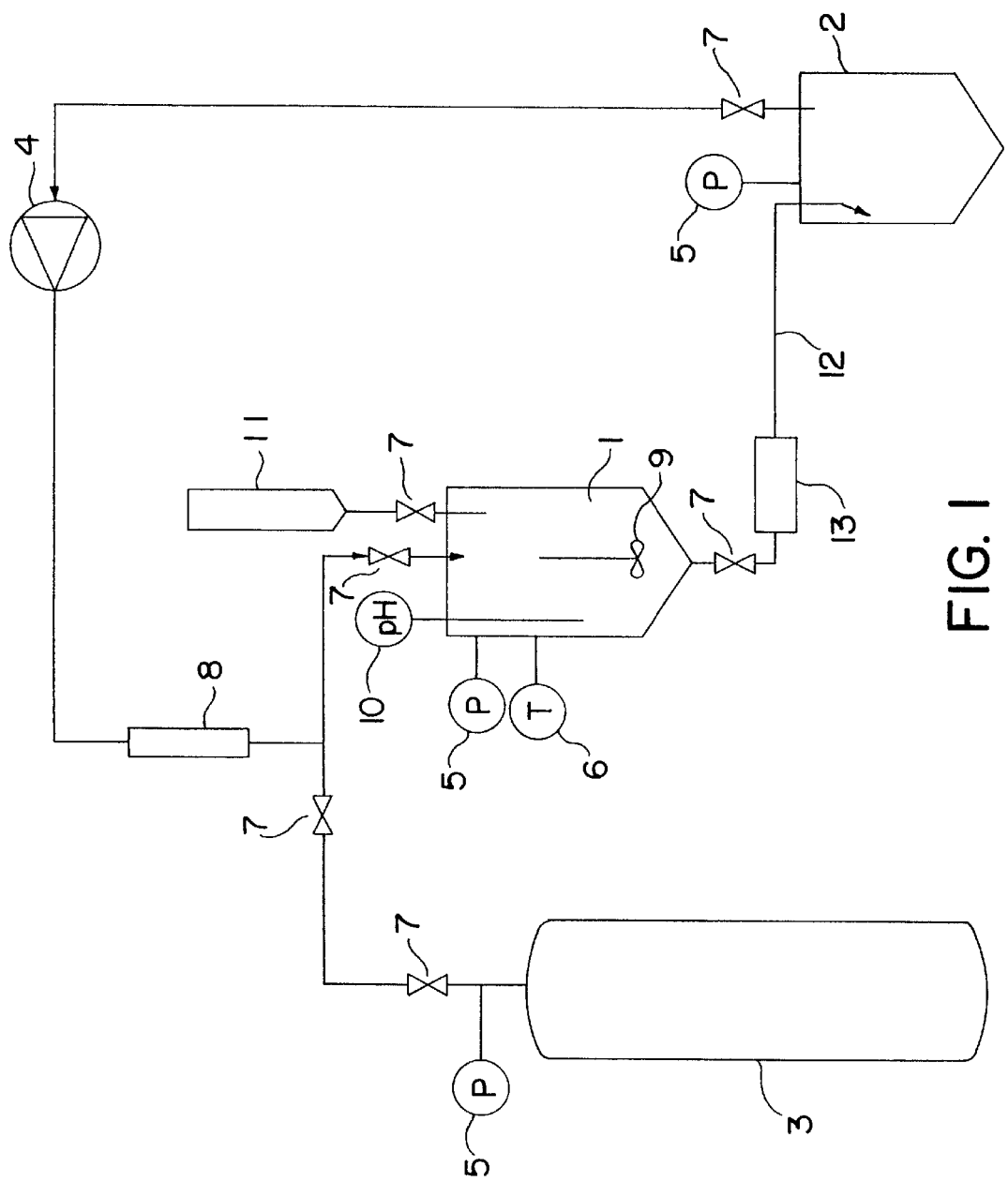
FIG. I

PROCESS FOR THE PREPARATION OF A METAL SALT OF CLAVULANIC ACID

This is a 35 USC §371 National Stage Application entry of PCT International Application No. PCT/EP98/02137, filed Apr. 2, 1998.

This invention relates to a process for the preparation of salts of clavulanic acid. In particular the invention relates to a process for the preparation of potassium clavulanate from salts of clavulanic acid with organic amines.

Clavulanic acid (3-(2-hydroxyethylidene)-7-oxo-4-oxa-1-azabicyclo [3.2.0] heptane-2-carboxylic acid) is a known beta-lactamase inhibitor, i.e. it and its compounds inhibit the beta-lactamase enzymes by means of which bacteria defend themselves against beta-lactam antibiotics such penicillins. Clavulanic acid, particularly in the form of its salts, can therefore be co-administered with such antibiotics, particularly amoxycillin and ticarcillin to overcome beta-lactamase mediated bacterial resistance.

Clavulanic acid is normally prepared by the fermentation of a microorganism which produces clavulanic acid, such as microorganisms belonging to various Streptomyces strains such as *S. clavuligerus* NRRL 3585, *S. jumoninensis* NRRL 5741, *S. katsurahamanus* IFO 13716 and Streptomyces sp. P 6621 FERM P2804 e.g. as described in JP Kokai 80-162993. The resulting aqueous broth may be subjected to conventional purification and concentration processes, for example involving filtration and chromatographic purification, such as disclosed in GB 1508977 and JP Kokai 80-62993, before extraction of the aqueous solution with an organic solvent to yield a solution of crude clavulanic acid in the organic solvent. Alternatively a "whole broth extraction" process of generally known type may be used to yield a solution of crude clavulanic acid in the organic solvent.

To isolate the clavulanic acid from the organic solvent solution one known procedure is to first convert the clavulanic acid into a salt with an organic amine. EP 0026044 discloses the use of the tertiary butylamine ("t-BA") salt of clavulanic acid as a useful intermediate in the isolation of clavulanic acid. This salt may be formed by reaction of the solution of crude clavulanic acid in the organic solvent with tertiary butylamine, resulting in formation of the salt which can be isolated, for example as a crystalline solvate e.g. of acetone. This tertiary butylamine salt of clavulanic acid may be converted to potassium clavulanate by reaction with for example a precursor compound such as potassium 2-ethylhexanoate in a suitable solvent medium such as isopropanol.

Numerous other amines may be used in processes for isolation of clavulanic acid. PT.94.908 describes the use of tri-(lower alkyl)amine, e.g. triethylamine, salts and the dimethylaniline salts of clavulanic acid in a purification process for clavulanic acid in which the triethylamine salt of clavulanic acid is formed and is then converted into a silyl diester of clavulanic acid. EP 0887178A discloses a process for the purification of clavulanic acid in which organic amines may be used to form an intermediate amine salt with clavulanic acid in an impure solution. WO 93/25557 discloses an extensive series of amines which can be used. WO 96/33197, EP 0562583A, WO 94/21647, EP 0594099A, WO 94/22873, WO 95/23870, GB 2298201A and WO 96/20188 all disclose various other amines which can be used in this way.

Clavulanic acid and its salts such as potassium clavulanate are unstable, moisture sensitive compounds, and known processes for their preparation all suffer to a greater or lesser extent from problems of degradation resulting from such instability and hydrolysis. It is an object of this invention to provide an improved process which to some extent at least overcomes these problems.

According to this invention a process for the preparation of a metal salt of clavulanic acid comprises the reaction between an organic amine salt of clavulanic acid and a metal salt precursor compound, the reaction taking place in a liquid medium which comprises a liquid fluorinated and/or chlorinated hydrocarbon.

In a preferred embodiment of this invention the metal salt of clavulanic acid prepared by this process is potassium clavulanate.

The amine salt may be any amine salt which may be used in a process of the above-described type where clavulanic acid is first isolated as a salt of the amine which is then converted into a metal salt such as potassium clavulanate. In a preferred embodiment the organic amine salt of clavulanic acid is the t-BA salt of clavulanic acid. Other suitable amine salts include the following. (When alkyl groups or substituted alkyl groups are referred to herein unless otherwise defined herein they may suitably contain 1 to 6 carbon atoms in the alkyl system.) Those disclosed in WO 93/25557, i.e an amine of formula (I):

(I)

as an intermediate in a process for the preparation of clavulanic acid or pharmaceutically acceptable salts and esters thereof, wherein $R^1$, $R^2$ and $R^3$ are selected according to the following options:

(1) $R^1$ being an optionally substituted cyclic group of general formula:

where m is zero or an integer 1 to 5, R is an optionally substituted aliphatic hydrocarbon ring system containing from 3 to 8 ring carbon atoms, $R^4$ is hydrogen or alkyl, amino- or hydroxy-substituted alkyl or substituted amino-substituted alkyl, or a group of the same general formula or $R^1$ above:, $R^2$ and $R^3$ may be selected from the same groups from which $R^1$ is selected, or from hydrogen, alkyl, alkenyl, amino- or hydroxy-substituted alkyl or alkenyl, or substituted amino-substituted alkyl or alkenyl: or (2) each of $R^1$, $R^2$ and $R^3$ are the same or different and are independently selected from hydrogen, alkyl, alkenyl, amino—or hydroxy- or alkoxy-substituted alkyl or alkenyl, or substituted amino-substituted alkyl or alkenyl, but with the exception of t-butylamine, s-butylamine, N,N-dimethylethylamine, 1,2dimethylpropylamine, neopentylamine and 2-amino-3,3-dimethylbutane: or (3) $R^1$ being an optionally substituted aryl group of general formula:

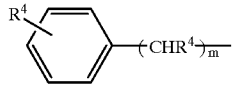

where $R^4$ is hydrogen or one or more substituents, and m is zero or an integer 1 to 5, and $R^2$ and $R^3$ are independently selected from hydrogen, allyl, amino- or hydroxy-substituted alkyl or substituted—amino-substituted alkyl or groups of the same general formula as $R^1$: or (4) R¹ and R², and optionally R³, together with the nitrogen atom shown being the residue of an optionally substituted heterocyclic ring system including the nitrogen atom as a ring member, and optionally including one or more additional ring hetero atoms, and if R³ is not part of the ring system it is independently selected from hydrogen, alkyl, amino- or hydroxy-substituted alkyl or substituted amino-substituted alkyl: or (5) R¹ being a group of general formula:

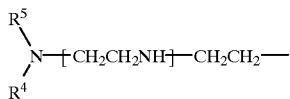

where R⁴ and R⁵ are independently hydrogen, alkyl, amino-substituted alkyl or substituted amino-substituted alkyl, and R² and R³ are independently selected from hydrogen, alkyl, amino- or hydroxy-substituted alkyl or substituted amino-substituted alkyl, and m is zero or an integer 1 to 5: or (6) One or both of R¹ and R² are hydrogen and R³ represents the residue of an amino acid in which the carboxylate group of the amino acid may be esterified or in the form of an amide.

Examples of such amines include cyclopentylamine, cyclohexylamine, cycloheptylamine, NN-imethylcyclohexylamine, dicyclohexylamine, adamantylamine, NN-diethylcyclohexylamine, N-isopropylcyclohexylamine, N-methylcyclohexylamine, cyclopropylamine, cyclobutylamine, norbornylamine, dehydroabietylamine, t-octylamine, (ie 2-amino-2,4,4-timethylpentane), t-amylamine, 1-hydroxy-2-methyl-2-propylamine, tri-n-propylamine, tri-n-octylamine, tri-n-butylamine, dimethylamine, i-propylamine, di-n-hexylarnine, di-nbutylamine, diethylamine, 2-aminoethanol, NN-diethylethanolamine, NN-dimethylethanolamine, ethanolamine, n-butylamine, n-hexylamine, noctadecylamine, N-ethylethanolamine, 1-hydroxyethylamine, diethanolamine, NNdimethylethanolamine, N-ethyl diethanolamine, 1, 6-diamino hexane, triethanolamine, diisobutylamine, diisopropylamine, 2-methoxyethylamine, hydroxylamine, ammonia, methylamine, ethylamine, n-propylamine, n-butylamine, n-pentylamine, n-hexylamine, n-heptylamine, n-octylamine, n-nonylamine, ndecylamine, n-undecylamine, n-dodecylamine, n-prop-2-ylamine, n-but-2-ylamine, n-pent-2-ylamine, n-hex-2-yl-amine, n-hept-2-ylamine, n-oct-2-ylamine, n-non-2ylamine, n-dec-2-ylamine, n-undec-2-ylamine, n-dodec-2-ylamine, n-hex-3-ylamine, n-hept-3-ylamine, n-oct-3-ylamine, n-non-3-ylamine, n-dec-3-yl-amine, n-undec-3ylamine, n-dodec-3-ylamine, n-octylamine, n-non-4ylamine, n-dec-4-ylamine, nundec-4-ylamine, n-dodec4-ylamine, n-non-5-ylamine, n-undec-5-ylamine, ndodec-5-ylamine, and n-octadecylamine, 1-phenylethylamine, p-toluidine, paminobenzoic acid, p-bromoaniline, ethyl-4-aminobenzoate (ie benzocaine), benzylamine, diphenylamine, p-methylaminobenzene sulphonamide, m-nitroaniline, N,N'-dibenzylethylenediamine (ie benzathine), diphenylmethylamine, 4-methylbenzylamine, 4-phenylbutylarnine, piperidines and optionally substituted piperidines, for example where the substituents are selected from alkyl, hydroxyaLkyl, halogen, amino, substituted amino and amino-substituted alkyl, e.g N-ethyl piperidine, 2,6-dimethyl piperidine, 2-methyl-N-hydroxypropyl piperidine (ie cyclo-methycane), 4-methyl piperazine, 1-methyl-4-phenyl piperazine, N-ethyl morpholamine, hexamethylenimine, pyridine, 2-prQpylpyridine, 3-chloro-2aminopyridine, morpholamine, 1,5-diazabicyclo [4, 3, 0] non-S-ene, 1,4-diazabicyclo [2, 2, 2] octane, pyrrolidone, quinuclidine, xanthinol, NNdiethylethylene diamine, NN'-diisopropylethylenediamine and triethylene tetramine, naturally occurring amino acids, such as arginine, ornithine, histidine, lysine, benzylglycine, 3-amino-3-methylbutanoic acid, L-ethyl lysinate, L-methyl histidinate, methyl N-carbobenzyloxy-L-lysinate, methyl L-phenylalanate, ethyl glycyl glycinate, ethyl p-hydroxy phenyl glycinate, ethyl p-hydroxy phenyl glycinate, ethyl glycinate, ethyl L-tyrosinate, p-methoxybenzyl aaminophenylacetate, n-butyl a-aminophenylacetate, methyl arginate, benzylglycine, benzyl phenylglycine, 1-nitrobenzyl phenyl glycine, n-butyl phenylglycine, pmethoxybenzyl phenylglycine, ethyl phenyl glycine, p-nitrobenzyl p-hydroxyphenylglycine, p-nitrobenzylserine, n-butyl serine, methyl arginine, dimethyl glutamate, pnitrobenzyl tyrosinate, p-nitrobenzyl glycinate, benzylglycinate, p-nitrobenzyl aamino-p-hydroxy-phenyl acetate, p-nitrobenzyl α-aminophenylacetate, ethyl aamino-p-hydroxy phenyl acetate, ethyl L-tyrosinate.

When the amine (I) contains more than one nitrogen aton the clavulanic acid may form a salt with one or more of the nitrogen atoms, for example as in NN'-diisopropylethylenediamine diclavulanate.

Of the amines last mentioned above, preferred amines are: phenylethylamine, t-amylamine, t-octylamine, 1-hydroxy-2-methyl-2-propylamine, cyclopentylamine, cycloheptylamine, 1-adamantanamine, N-ethylpiperidine, N'N'-diisopropylethylenediamine and NN-dimethylcyclohexylamine.

Those disclosed in WO 96/33197, i.e having the general formula (II):

where the substituents R¹, R², R³ and R⁴ are independently hydrogen, C$_{(1-8)}$ straight or branched alkyl, C$_{(2-4)}$ hydroxyalkyl or wherein the groups NR₁R₂ and NR₃R₄ jointly denote a heterocyclic group having 3 to 6 methylene groups optionally substituted with oxygen, sulphur or an imino group; and wherein R₅ denotes hydrogen or methyl, and n is an integer from 1 to 3. Examples of such last mentioned amines include symmetrical N,N'-alkylethylene diamines, such as N,N'-diisopropylethylenediamine, N,N'-diethylenediamine, N,N'-dibenzylethylenediamine, N,N,N', N'-tetramethylethylenediamine.

Those disclosed in EP 0562583 and WO 94/21647, i.e. of formula (II) with the additional possibilities that R¹, R², R³ and R⁴ may independently be an arylalkyl group, for example with the alkyl moiety being methyl or ethyl, and the aryl group, for example phenyl, which may be substituted, particularly in its para-position, with an alkyl e.g methyl, alkoxy e.g methoxy, nitro or halogen; a C$_{2-4}$ hydroxyalkyl group, a C$_{2-4}$ aminoalkyl group, for example substituted by a 1 to 4 carbon atom containing N-alkyl or N,N-dialkyl group; or R¹, R², R³ and R⁴ may together form an alkylene ring system with 3 to 6 methylene groups, in which one of these groups may be substituted or replaced by an oxygen or sulphur atom or an imino group.

Those disclosed in WO 94122873, i.e of formula (III):

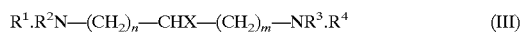

wherein R¹ and R² are each C$_{1-8}$ alkyl, C$_{3-8}$ cycloalkyl or C$_{3-8}$ cycloalkyl C$_{1-8}$ alkyl group, optionally having one or more inert substituents or being interlinked to form a ring of 4–7 ring atoms; $R^3$ and $R^4$ are each $C_{1-8}$ alkyl, $C_{3-8}$ cycloalkyl or $C_{3-8}$ cycloalkyl $C_{1-8}$ alkyl group, optionally having one or more inert substituents or being interlinked to form a ring of 4–7 ring atoms; X is hydrogen or a hydrogen bridge forming group; and m and n are each independently 0–5. Preferred moieties for such substituents are as disclosed in WO 94122873, and examples of such amines include N,N,N',N'-tetramethyl-1,2-diaminoethane, 1,3-bis(dimethylamino)2-propanol, N,N,N',N'-tetramethyl-1,4-diaminobutane, N,N,N',N'-tetramethyl1,6-diaminohexane, 1,2-dipiperidinoethane and dipiperidinomethane.

Those disclosed in GB2298201A, i.e of formula (IV):

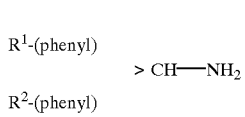

(IV)

wherein each of $R^1$ and $R^2$ independently denote hydrogen or a pharmaceutically acceptable substituent, for example lower alkyl, haloalkyl, alkoxyl or acyloxy. An example of such an amine is benzhydrylamine.

Those disclosed in WO 96/20199, i.e of formula (V):

(V)

wherein R1 is an alylene group (the term alkylene encompassing cycloalkylene and alkyl substituted cycloalkylene), optionally having one or more inert substituents; and each of R2 and R3 is a hydrogen atom or an alkyl group (which may be cycloalkyl), optionally having one or more inert substituents. An example of such an amine is bis-(2-dimethylaminoethyleether).

The contents of these forementioned patent publications are included herein in their entirety by way of reference.

Where the amine base contains two or more basic nitrogen atoms, one, or more than one up to all of these basic nitrogen atoms may be combined in the amine salt with a respective clavulanate ion.

The metal salt precursor compound may be a salt or salt-like compound, or a basic compound, of a metal cation with a suitable counter anion. The metal is suitably a pharmaceutically acceptable alkali metal such as sodium or particularly potassium, or an alkaline earth metal. The metal salt precursor compound may be a salt of the metal with an organic carboxylic acid, for example a salt of an alkanoic acid of formula (I):

(I)

wherein $R^{10}$ is an alkyl group, containing for example from 1 to 20 carbon atoms, preferably from 1 to 8 carbon atoms. Examples of suitable salts include acetate, propionate or ethylhexanoate salts, potassium 2-ethylhexanoate and sodium 2-ethylhexanoate being preferred. Alternatively the metal salt precursor compound may be a basic compound, for example a carbonate, bicarbonate or hydroxide of the metal.

It is preferred that a stoichiometric excess of the metal salt precursor compound over the organic amine salt of clavulanic acid is used to ensure complete reaction of the organic amine salt of clavulanic acid. For example around a 1.3:1 ratio of metal salt precursor compound : organic amine salt of clavulanic acid may be used.

The liquid medium is preferably a gas at ambient temperature but which can be liquefied at ambient temperature by pressure. Suitably the fluorinated and/or chlorinated hydrocarbon is a compound of formula CnHmXpYr where X is fluorine, Y is chlorine n and m are whole numbers, p and r are zero or whole numbers provided both p and r are not zero and (m+p+r) equals 2n+2. The liquid medium is preferably a fluorinated non-chlorinated hydrocarbon. Preferably the medium is a fluorinated non-chlorinated compound of formula $C_nH_mF_p$ where n, m and p are whole numbers and (m+p) equals 2n+2.

The lower and upper limits of n are determined more by the practical considerations of achieving a boiling point which is low enough to allow easy evaporation but not so low that high pressures are needed for liquefaction. For example a suitable boiling point for the liquid non-chlorinated fluorinated hydrocarbon is −10 to −50° C. at ambient atmospheric pressure, and typically n is between 1 and 10. Preferably in such a compound n is 2 or 3, preferably 2 so that the compound is an ethane, preferably p is 3, 4 or 5, especially 4 so that the compound is a tetrafluoroethane. A preferred fluorinated hydrocarbon is 1,1,1,2-tetrafluoroethane. Other suitable fluorinated/chlorinated hydrocarbons include fluoroform, methyl chloride, difluorodichloromethane, monofluoromethane, difluoromethane, trifluoromethane, pentafluoroethane, 1,1,1-trifluoroethane, 1,1difluoroethane, 1,1,1,2,3,3,3-heptafluoropropane, 1,1,1,2,2,3,3heptafluoropropane, 1,1,1,3,3,3-hexafluoropropane, 1,1,1,2,2-pentafluoropropane, 1,1,1,2,2,3-hexafluoropropane, 1,1,2,2,3,3-hexafluoropropane, and 1,1,1,2,3,3hexafluoropropane.

Such fluorinated/chlorinated hydrocarbons, particularly fluorinated nonchlorinated hydrocarbons have the advantages as media for the process of the invention that they are odourless and colourless gases at ambient temperature, liquefy at around 5 bar at ambient temperature, are chemically inert, are nonflammable, are non-toxic, are non-corrosive, have a neutral pH, are non-ozone depleting and are approved for use in food processing by the EEC.

The liquid medium may comprise a mixture of such fluorinated and/or chlorinated hydrocarbons, e.g a mixture of fluorinated non-chlorinated hydrocarbons, for example to achieve a convenient boiling point. The liquid medium may also include other organic solvents, for example to modify the polarity of the medium, and suitable such organic solvents include alcohols and ethers, for example $C_1$–$C_5$ aliphatic alcohols and ethers. Such organic solvents may be solvents for the metal salt precursor compound. When the metal salt precursor compound is a salt of the metal with an organic carboxylic acid, for example a salt of an alkanoic acid of formula (I) as mentioned above, such as potassium 2-ethyl hexanoate, suitable solvents include $C_1$–$C_5$ aliphatic alcohols such as isopropanol. Typically when a solvent for the metal salt precursor compound is present in the medium this may be present in a volume:volume ratio non-chlorinated fluorinated hydrocarbon: solvent for the metal salt precursor compound of 1:0–0.5, for example around 1:0.1–0.35.

It is preferred that the liquid medium also includes water as the presence of water appears to be desirable to achieve a crystalline product. Preferably water is present in the liquid medium in the range 0.1–3.0% v:v, but excessive amounts of water in the medium should be avoided to mininise aqueous degradation of the clavulanate salt product. Suitably ca. 0.5–2.5% v:v water may be present.

The reaction may be carried out over a broad concentration range of the organic amine salt of clavulanic acid, and the consequent concentration of the metal salt precursor compound as mentioned above. For example the concentration of the amine salt in the medium may lie in the range 0.05–5M.

In one form of the process of the invention the amine salt of clavulanic acid may be dissolved or suspended in an organic solvent, which may be a solvent for the metal salt precursor compound, in a suitable reactor vessel. The reactor vessel may then be charged with the fluorinated hydrocarbon solvent and pressurised to a pressure at which the fluorinated hydrocarbon solvent is a liquid, e.g. typically ca 4–6 bar. With the resulting solution or suspension of the amine salt may then be mixed a solution or suspension of the metal salt precursor compound, for example in a solvent as described above.

As explained above the reaction medium should contain a trace of water, and this may be included in the solution or suspension of the amine salt, or in the solution or suspension of the metal salt precursor compound added thereto, or water may be added to the reaction mixture. Metal salts of clavulanic acid are generally insoluble in the type of liquid medium resulting from this form of the process and the product metal salt of clavulanic acid will normally precipitate out from the reaction medium, so that it can easily be isolated by filtration. In the case of potassium clavulanate such a precipitate may comprise the known needle or rosette crystal forms. The filtered product may then be washed, for example with the fluorinated hydrocarbon. When the fluorinated hydrocarbon is a gas at room temperature excess fluorinated hydrocarbon may then conveniently be removed by reduction of the pressure in the reactor or filter.

In the above-described form of the process, if the metal salt precursor compound is a salt of an alkanoic acid of an acid of formula (1), for example potassium 2-ethylhexanoate, then the solution of the precursor compound may be made by dissolving the compound in a suitable solvent, or alternatively the precursor compound may be prepared in situ by reaction between a suitable metal-containing base such as potassium hydroxide and the parent acid, such as 2-ethyl hexanoic acid in the solvent.

Suitable apparatus for performing the process of the invention will be apparent to those skilled in the art. One suitable apparatus comprises a reaction vessel in which the reaction can take place, which can be charged with the fluorinated hydrocarbon and with the reagents and any other solvents, water etc. from appropriate sources, and which can be pressurised to a pressure at which the fluorinated hydrocarbon is a liquid, a receiver in fluid communication with the reaction vessel and into which liquid medium from the reaction vessel may be transferred after the reaction has taken place, with a filter between and in fluid communication with the reaction vessel and receiver, and which can retain particles of the product metal salt of clavulanic acid. Preferably the reaction vessel and receiver are also capable of evacuation so that the fluorinated hydrocarbon can be easily evaporated off, and the apparatus also preferably includes a compressor to return the fluorinated hydrocarbon to the source or to the reactor. Within such a general description various constructions of apparatus will be apparent to those skilled in the art.

The method of the invention has the advantages that the reaction is simple and rapid, can achieve yield improvements, and reduction in solvent usage.

The invention will now be described by way of example with reference to FIG. 1 which schematically shows a reaction assembly.

EXAMPLE 1

Equipment

The equipment used for this work consisted of a 5 L reaction/extraction vessel (1) and a 5 L receiver/evaporation vessel (2), both vessels being jacketed, a 1,1,1,2tetrafluoroethane gas cylinder (3) and compressor (4). The whole was connected together with a system of pipes, pressure gauges (5), thermometers (6), valves (7), condenser (8), etc. to allow a multi task function. The reactor was equipped with a stirrer (9), a pH port (10) and a burette (11) designed to introduce reagents whilst the system was pressurised. After materials were charged into the reaction/extraction vessel, the whole system could be evacuated then 1,1,1,2-tetrafluoroethane gas charged into the reaction/extraction (1) to a pressure of 5 bar. Reagents could then be introduced via the burette (11). When the reaction or extraction was complete, the mixture could be discharged to the evaporator (2) via a transfer line (12) and an inline filter (13). The 1,1,1,2-tetrafluoroethane gas could be evaporated using the compressor (4) and condensed into liquid form in condenser (8), and could be either charged back into the cylinder (3) or recycled through the reactor/extractor (1).

Experimental Data

Method: Expts. 1–3 t-BA clavulanate was charged to the reactor followed by isopropanol and water. The vessel was sealed and evacuated then 1,1,1,2-tetrafluoroethane was charged until system pressure equilibrated at 5 bar. Potassium ethyl hexanoate ("KEH")/isopropanol ("EPA") was charged to the burette then added to the reactor whilst stirring over 30 minutes. At the end of a further 20 minute stirring, the contents of the reactor where transferred to the receiver via the in-line filter. 1,1,1,2-tetrafluoroethane gas was compressed back into the reservoir cylinder. The filtered product in the reactor was slurried twice in 1,1,1,2-tetrafluoroethane to remove isopropanol residues and associated impurities. This had the effect of producing dry product with very little solvent and water contamination.

Method: Expts. 4 and 5

2-ethyl hexanoic acid (101 g) was charged into a beaker containing isopropanol (300 ml). The solution was chilled to 10° C. and potassium hydroxide (40.8 g) was added whilst stirring vigorously. When all the potassium hydroxide was dissolved, isopropanol was added to make up a total volume of 420 ml. This solution was transferred to the burette vessel of the 1,1,1,2-tetrafluoroethane rig. t-BA clavulanate (154 g) and isopropanol (500 ml) were charged to the reaction vessel and continued as above.

Results

All products passed on appearance, water content and purity. Stability studies using DVS showed poor results for Expt. 2 suggesting that water presence during the reaction is essential to crystal formation. The stability of the product from Expt. 4 was very good and Expt.5 produced products of exceptional stability.

The following table shows data obtained from reactions using 2.5L 1,1,1,2tetrafluoroethane and standard potassium ethyl hexanoate/isopropanol solution (concentration=2N and water content=2%)

| Expt No. | Wt t-BA clav. g | Vol IPA ml | Vol H$_2$O ml | Wt KEH g | Loss in ML % | Yield % | Purity % pfa |
|---|---|---|---|---|---|---|---|
| 1 | 250 | 700 | 30 | 191.7 | 1.2 | 96.5 | 81.8 |
| 2 | 150 | 500 | 0 | 116.2 | 1.2 | 96.7 | 81.1 |
| 3 | 150 | 500 | 10 | 116.9 | 1.4 | 98.1 | 81.8 |

The following data was obtained from reactions using 2.5L 1,1,1,2tetrafluoroethane and wet potassium ethyl hexanoate/ isopropanol solution which was prepared by mixing equi-molar amounts of potassium hydroxide and 2-ethylhexanoic acid in isopropanol with no azeotropic distillation:

| Expt No. | Wt t-BA clav. g | Vol IPA ml | Vol H$_2$O ml | Wt KEH g | Loss in ML % | Yield % | Purity % pfa |
|---|---|---|---|---|---|---|---|
| 4 | 150 | 500 | 0 | 117.0 | 1.2 | 96% | 82.3 |
| 5 | 154 | 500 | 4 | N/A | 1.6 | N/A | 81.6 |

What is claimed is:

1. A process for the preparation of a metal salt of clavulanic acid which comprises the reaction between an organic amine salt of clavulanic acid and a metal salt precursor compound, the reaction taking place in a liquid medium which comprises a liquid fluorinated and/or chlorinated hydrocarbon.

2. A process according to claim 1, characterised in that the organic amine salt of clavulanic acid is the salt of clavulanic acid with tertiary-butylamine, a N,N'-substituted diamine, an N,N'-monosubstituted symmetric diamines or N,N'-monosubstituted symmetric alkylethylene diamine or tertiary octylamine.

3. A process according to claim 1, characterised in that the metal salt precursor compound is a salt or salt-like compound, or a basic compound, of a metal cation with a counter anion.

4. A process according to claim 3 characterised in that the metal in the metal salt precursor compound is potassium or sodium.

5. A process according to claim 4 characterised in that the metal salt precursor compound is a salt of the metal with an organic carboxylic acid of formula (I):

$$R^{10}\text{---}CO_2H \quad (I)$$

wherein $R^{10}$ is an alkyl group containing from 1 to 20 carbon atoms.

6. A process according to claim 5 characterised in that the metal salt precursor compound is potassium 2-ethylhexanoate.

7. A process according to claim 1 characterised in that the liquid medium is a gas at ambient temperature which can be liquefied at ambient temperature by pressure.

8. A process according to claim 7 characterised in that the boiling point for the liquid fluorinated and/or chlorinated hydrocarbon is −10 to −50° C. at ambient atmospheric pressure.

9. A process according to claim 1 characterised in that the fluorinated and/or chlorinated hydrocarbon is a compound of formula CnHmXpYr where X is fluorine, Y is chlorine n and m are whole numbers, p and r are zero or whole numbers provided both p and r are not zero and (m+p+r) equals 2n+2.

10. A process according to claim 1 characterised in that the liquid medium is a fluorinated non-chlorinated hydrocarbon.

11. A process according to claim 9 characterised in that the medium is a fluorinated non-chlorinated compound of formula $C_nH_mF_p$ where n, m and p are whole numbers and (m+p) equals 2n+2.

12. A process according to claim 11 characterised in that n is 2 or 3.

13. A process according to claim 1 characterised in that the fluorinated and/or chlorinated hydrocarbon is selected from 1,1,1,2-tetrafluoroethane, fluoroform, methyl chloride, difluorodichloromethane, monofluoromethane, difluoromethane, trifluoromethane, pentafluoroethane, 1,1,1-trifluoroethane, 1,1-difluoroethane, 1,1,1,2,3,3,3-heptafluoropropane, 1,1,1,2,2,3,3-heptafluoropropane, 1,1,1,3,3,3-hexafluoropropane, 1,1,1,2,2-pentafluoropropane, 1,1,1,2,2,3-hexafluoropropane, 1,1,2,2,3,3-hexafluoropropane, and 1,1,1,2,3,3-hexafluoropropane.

14. A process according to claim 1 characterised in that the liquid medium comprises a mixture of fluorinated and/or chlorinated hydrocarbons.

15. A process according to claim 1 characterised in that the metal salt of clavulanic acid prepared in the reaction is potassium clavulanate.

* * * * *